United States Patent [19]

Gurak et al.

[11] Patent Number: 5,146,042
[45] Date of Patent: Sep. 8, 1992

[54] DESULFURIZATION OF LIGHT OLEFINS

[75] Inventors: Nur R. Gurak, Sarnia, Canada; Jacques M. Hamard, Rixensart, Belgium

[73] Assignee: Exxon Chemical Patents Inc., Linden, N.J.

[21] Appl. No.: 742,257

[22] Filed: Aug. 8, 1991

[51] Int. Cl.$^5$ .................... C07C 7/00; C01B 17/00
[52] U.S. Cl. .................... 585/867; 585/864; 423/243; 423/245.2
[58] Field of Search .................. 585/809, 867, 864; 423/243, 245.2

[56] References Cited

U.S. PATENT DOCUMENTS

| | | | |
|---|---|---|---|
| 2,577,617 | 12/1951 | Hudig | 585/867 |
| 3,315,003 | 4/1967 | Khelghatian | 585/809 |
| 4,444,987 | 4/1984 | Brownell et al. | 585/850 |
| 4,835,338 | 5/1989 | Liu | 585/823 |

Primary Examiner—Anthony McFarlane
Assistant Examiner—Nhat Phan

[57] ABSTRACT

This invention provides a simple process for the removal of organo sulfide contaminants from lower $C_2$ to $C_4$ olefin feedstocks comprising washing the lower olefin containing the sulfide contaminant with a liquid $C_6$ or higher olefin which is a solvent for the sulfur contaminant. The washing process tends to extract a substantial quantity of the sulfur contaminant from the lower olefin. The lower olefin is then separated from the higher olefin solution by evaporation or fractional distillation. The process provides for removal of greater than 90% by weight of organic sulfides present in lower olefin feedstocks.

11 Claims, 1 Drawing Sheet

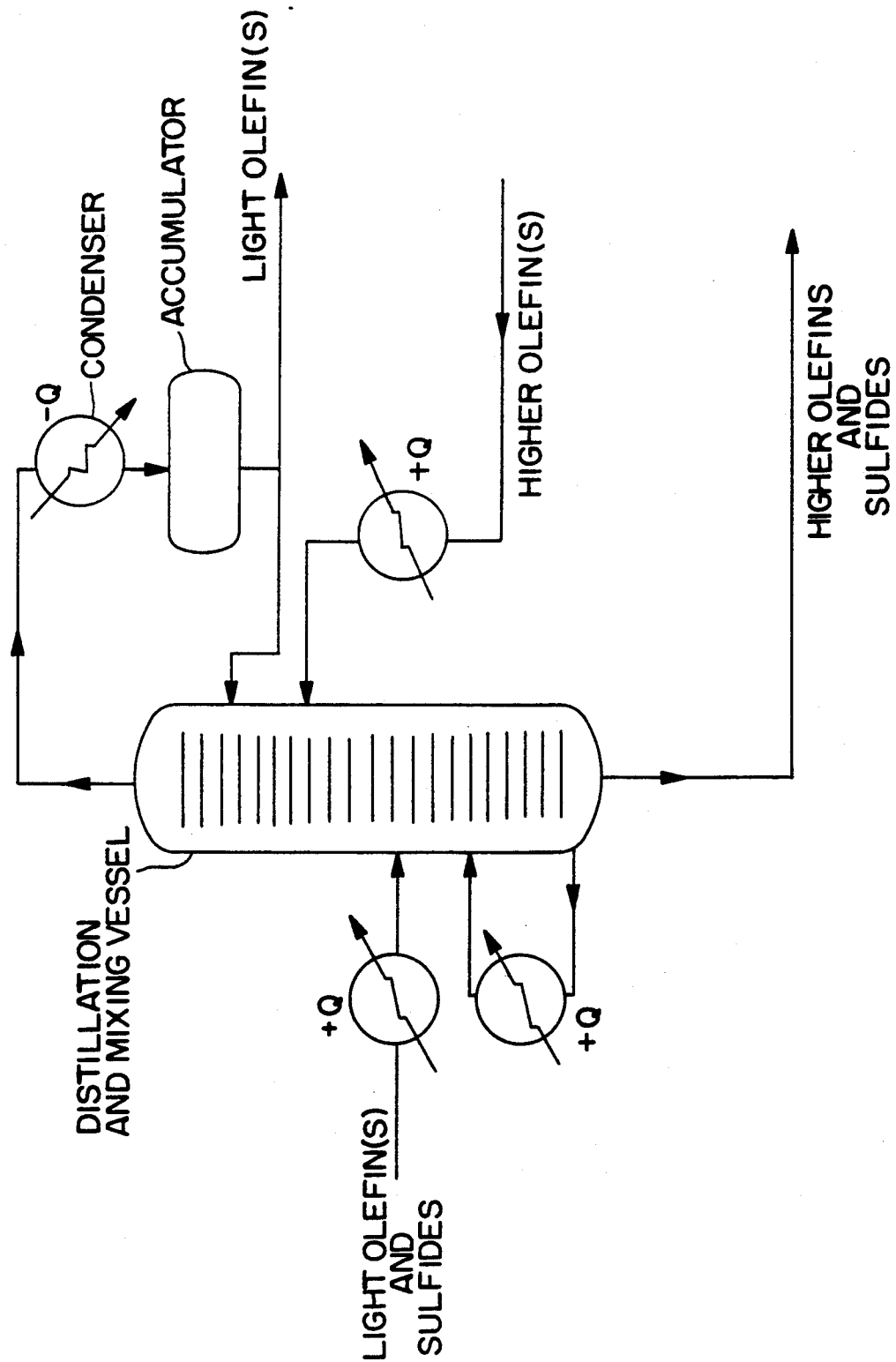

DESULFURIZATION OF LIGHT OLEFINS

FIELD OF THE INVENTION

The present invention relates to a process for significantly reducing trace amounts of sulfur contaminants present in $C_2$ to $C_4$ olefins.

DESCRIPTION OF RELATED ART

Light $C_2$ to $C_4$ olefins are produced as a product of petroleum cracking and fractional distillation of refinery gases. Small quantities of sulfur contaminants, e.g. organic sulfides and polysulfides, are normally present in the olefin feedstocks as a consequence of a carryover of some sulfur contaminants present in the parent petroleum or gaseous feedstock and/or as a consequence of contamination during processing. The presence of these sulfur contaminants can lead to undesirable side reactions when the light olefins are further processed to form other species such as oligomers, polymers, alcohols and the like, resulting in lower yields of these desired end products and higher catalyst consumption. The removal of the offending sulfur contaminants prior to further processing of the light olefins is therefore desirable.

One known technique for the removal of sulfides from olefins involves contacting the olefin with a nickel hydrogenation catalyst at temperatures of 300° F. or above. The nickel catalyst may be a Raney nickel or an impregnated or coprecipitated nickel type catalyst which complexes the sulfide contaminant present in the olefin.

While this approach to sulfur removal has been demonstrated with higher olefins,, e.g., $C_5$ to $C_{12}$ olefins, it is not particularly suited for sulfur removal from the lower olefins because of the tendency of the lower olefins, particularly $C_2$ and $C_3$ olefins, to form dimers when contacted with nickel at the required high temperatures.

A different technique for removal of sulfur contaminants present in liquid hydrocarbon distillates is disclosed in French published application 2152384. This process involves washing the sulfur containing distillate with a solvent such as a mixture of phenol and water, which solvent is a better solvent for the sulfur contaminant then the distillate, and then separating the distillate from the solvent/sulfur mixture.

SUMMARY OF THE INVENTION

This invention provides a simple process for the removal of organo sulfide contaminants from lower $C_2$ to $C_4$ olefin feedstocks comprising washing the lower olefin containing the sulfide contaminant with a liquid $C_6$ or higher olefin which is a solvent for the sulfur contaminant. The washing process tends to extract a substantial quantity of the sulfur contaminant from the lower olefin. The lower olefin is then separated from the higher olefin solution by evaporation or fractional distillation. The process provides for removal of greater than 90% by weight of organic sulfides present in lower olefin feedstocks.

BRIEF DESCRIPTION OF THE DRAWING

FIG. 1 is a schematic diagram illustrating the process of this invention for removal of sulfides from light olefins using a higher olefin wash.

DETAILED DESCRIPTION OF THE INVENTION

The process of the invention may be carried out by introducing the sulfur contaminated lower olefin such as ethylene, propylene or butene in gaseous or liquid form into a vessel such as a container, extraction tower or column equipped with heating and/or pressurizing means,, which is at least partially filled with the liquid $C_6$ or higher olefin extractant.

In one embodiment, the lower olefin in gaseous form is introduced near the base of the vessel and allowed to bubble through a circulating current of the liquid higher olefin. Temperature and pressure conditions within the vessel are such that the lower olefin remains gaseous and the higher olefin remains liquid. The gaseous lower olefin vapors pass through the liquid solution during which time a significant content of the sulfide contaminant transfers from the gaseous lower olefin into the liquid higher olefin. The lower olefin vapors exit the solution and pass to the upper portion of the vessel where they may be collected and fed to a condenser.

In another embodiment, the lower olefin is introduced into the vessel under pressure in liquid form. The liquid olefins are mixed using an agitator or similar device such that a single phase solution of both olefins is formed. In this embodiment,, the higher olefin content of the mixture is at least about 20% by volume, more preferably at least about 40% by volume. Again, the sulfide contaminants pass from the lower olefin to the higher olefin in which they are more soluble. After a suitable period of time, the vessel is depressurized and the lower olefin may be extractively distilled by heating the vessel to distill off the lower olefin in vapor form. Alternatively, this process is subject to continuous operation wherein the contents of the vessel may be continuously discharged into a second zone where separation by fractional distillation takes place. One such configuration is shown by the schematic diagram of FIG. 1. The symbol "Q" is indicative of heat transferred.

The preferred higher olefin extractants which may be employed in the present invention are $C_6$ to $C_{16}$ monoolefins and include hexenes heptenes, octenes and nonenes. These materials generally have boiling points at atmospheric pressure in excess of 60° C., whereas the contaminated lower olefins have boiling points less than about 4° C.

Sulfur contaminants which may be removed in accordance with this invention include $C_1$ to $C_4$ sulfides and polysulfides. Typical olefin contaminants include dimethyl sulfide, diethyl sulfide, dipropyl sulfide and methylethyl sulfide.

The higher olefin fraction containing the sulfur contaminant extracted from the lower olefin fraction may subsequently be itself desulfurized using any suitable technique such as by contacting it with a nickel hydrogenation catalyst by the prior art process described above. Thus, the process of the present invention is amenable to a continuous recycle of desulfurized higher olefin back into the extraction process.

The extraction process is not temperature dependent and may be conducted at ambient temperature or at temperatures of up to about 160° C. depending on the pressure of the extraction process.

The following examples are illustrative of the invention.

EXAMPLE 1

300 cc of liquid propylene was mixed with methylethyl sulfide to yield a sulfur content of 10 weight parts per million (wppm). The contaminated propylene was introduced in gaseous form into the base of a container and bubbled through 200 cc of heptene which itself contained 23.9 wppm of sulfur contaminant. The sulfur content of the heptene was measured before and after the experiment. Also the propylene feed cylinder was thoroughly washed with heptene and the heptene wash sulfur content was measured.

EXAMPLE 2

A 50 cc portion of the contaminated propylene of Example 1 and 50 cc of nonene were introduced into a vessel (sight glass) and pressurized to 150 psi. The contents were shaken vigorously for 10 minutes and allowed to stand for 7 hours. No distinct phase separation of the propylene and nonene was observed, indicating that the propylene and nonene formed a single liquid phase solution.

The vessel was then depressurized and the propylene was distilled off.

Analysis of the sulfur content of the heptene and nonene, including the content from the feed cylinder washings, both before and after the treatment of Examples 1 and 2 indicated an increase in sulfur content in these olefins corresponding to greater than 90% removal of the sulfur contaminants originally present in the propylene feed.

What is claimed is:

1. A process for reducing the sulfide content present in lower $C_2$ to $C_4$ olefin feedstocks comprising contacting said lower olefin which contains an organo sulfide contaminant with a liquid $C_6$ or higher olefin in which said sulfide contaminant is soluble for a period of time sufficient to extract a substantial portion of the sulfide contaminant, and separating said lower olefin from the liquid $C_6$ or higher olefin solution.

2. The process of claim 1 wherein said lower olefin is in gaseous form and is bubbled through a solution of said liquid higher olefin.

3. The process of claim 1 wherein said lower olefin is in liquid form and is mixed with said liquid higher olefin to form a single liquid phase solution.

4. The process of claim 3 wherein said lower olefin is separated from said higher olefin solution by fractional distillation.

5. The process of claim 1 wherein said lower olefin is propylene.

6. The process of claim 1 wherein said higher olefin is a $C_6$ to $C_{16}$ olefin.

7. The process of claim 6 wherein said higher olefin is a heptene.

8. The process of claim 6 wherein said higher olefin is a nonene.

9. The process of claim 6 wherein said higher olefin is an octene.

10. The process of claim 1 wherein said sulfide contaminant comprises a $C_1$ to $C_4$ sulfide or polysulfide.

11. The process of claim 10 wherein said sulfide contaminant is methylethyl sulfide.

* * * * *